United States Patent
Kim et al.

(10) Patent No.: US 8,901,294 B2
(45) Date of Patent: Dec. 2, 2014

(54) MRI CONTRAST AGENT HAVING GADOLINIUM COMPLEX

(75) Inventors: Tae-Jeong Kim, Gyeongsan-si (KR); Yong Min Chang, Daegu (KR); Hee-Kyung Kim, Daegu (KR); Sung-Wook Gu, Daegu (KR)

(73) Assignee: Kyungpook National University Industry-Academic Cooperation Foundation (KR)

( * ) Notice: Subject to any disclaimer, the term of this patent is extended or adjusted under 35 U.S.C. 154(b) by 0 days.

(21) Appl. No.: 13/876,904

(22) PCT Filed: Dec. 21, 2010

(86) PCT No.: PCT/KR2010/009151
§ 371 (c)(1),
(2), (4) Date: Mar. 29, 2013

(87) PCT Pub. No.: WO2012/043933
PCT Pub. Date: Apr. 5, 2012

(65) Prior Publication Data
US 2013/0231475 A1   Sep. 5, 2013

(30) Foreign Application Priority Data
Sep. 30, 2010 (KR) .......... 10-2010-0095471

(51) Int. Cl.
*C07D 257/02* (2006.01)
*C07F 5/00* (2006.01)
*A61K 49/10* (2006.01)

(52) U.S. Cl.
CPC .............. *C07F 5/00* (2013.01); *C07D 257/02* (2013.01); *A61K 49/106* (2013.01)
USPC .......................................... 540/465; 540/474

(58) Field of Classification Search
CPC ....... C07D 257/02; C07F 5/00; A61K 49/106
USPC ................................................ 540/465, 474
See application file for complete search history.

(56) References Cited

U.S. PATENT DOCUMENTS

2010/0227794 A1*   9/2010   Yezdimer et al. .............. 514/2

OTHER PUBLICATIONS

International Search Report—PCT/KR2010/009151 dated Nov. 17, 2011.
N. Raghunand, et al., Design, Synthesis, and Evaluation of 1,4,7,10-Tetraazacyclododecane-1,4,7-triacetic Acid Derived, Redox-Sensitive Contrast Agents for Magnetic Resonance Imaging, Journal of Medicinal Chemistry Article, 2010, pp. 6747-6757.
N. V. Amirkhanov, et al., Design of (Gd-DO3A)n-Polydiamidopropanoyl-Peptide Nucleic Acid-D(Cys-Ser-Lys-Cys) Magnetic Resonance Contrast Agents, Biopolymers vol. 89, 2008, pp. 1061-1076.
A. Vaidya, et al., Contrast-enhanced MRI-guided photodynamic cancer therapy with a pegylated bifunctional polymer conjugate, NIH Public Access Author Manuscript, 2008, pp. 1-16.
G. Liu, et al., Design and Characterization of a New Irreversible Responsive PARACEST MRI Contrast Agent that Detects Nitric Oxide, Magnetic Resonance in Medicine 58, 2007, pp. 1249-1256.
R. Xu, et al., In Vivo Evaluation of a PAMAM-Cystamine-(Gd-DO3A) Conjugate as a Biodegradable Macromolecular MRI Contrast Agent, Experimental Biology and Medicine, 2008, pp. 1081-1089.
Z. Jaszberenyi, et al., Physicochemical and MRI characterization of Gd3+-loaded polyamidoamine and hyperbranched dendrimers, J Biol Inorg Chem, 2007, pp. 406-420.

* cited by examiner

*Primary Examiner* — Erich A Leeser
(74) *Attorney, Agent, or Firm* — Cantor Colburn LLP

(57) ABSTRACT

The present invention relates to a magnetic resonance imaging (MRI) contrast agent including a gadolinium complex, more particularly to a DO3A-tranexamic acid or its ester compound, which is represented by the Chemical Formula 1. A DO3A-tranexamic acid or its ester compound may be prepared according to the present invention and a gadolinium complex may be prepared using the compound. An MRI contrast agent including the gadolinium complex prepared according to the present invention as an active ingredient has higher relaxivity as compared to the currently commercially available contrast agent. In addition, the MRI contrast agent according to the present invention has bifunctionality of liver-specific and blood-pool contrasting effect. Accordingly, since the MRI contrast agent including the gadolinium complex according to the present invention satisfies the key properties required for a contrast agent for MRI, it can be widely used as an MRI contrast agent and can provide enhanced contrasting effect as compared to the existing contrast agent.

10 Claims, 8 Drawing Sheets

MRI CONTRAST AGENT HAVING GADOLINIUM COMPLEX

TECHNICAL FIELD

The present invention relates to a magnetic resonance imaging (MRI) contrast agent comprising a gadolinium complex, more particularly to a DO3A-tranexamic acid or its ester compound, which is represented by the Chemical Formula 1.

BACKGROUND ART

Magnetic resonance imaging (MRI) is a medical imaging technique used to obtain anatomical, physiological and biochemical information based on relaxation of proton spin in a magnetic field. It is one of excellent imaging techniques capable of visualizing the body organs of a human or an animal in real time in a non-invasive manner.

In the field of bioscience and medicine, a substance is injected from outside to enhance contrast in MRI. This substance is called a contrast agent. On an MRI image, the contrast between tissues occurs because relaxation whereby the nuclear spin of water molecules in a tissue returns to the equilibrium state is different from tissue to tissue. The contrast agent affects the relaxation, thereby altering the relaxation times in different tissues, and induces the change in MRI signals, thereby enhancing contrast between tissues. There occurs difference in precision depending on the feature and function of the contrast agent and the subject to which it is injected. The contrast enhanced using the contrast agent allows more clear imaging by intensifying or weakening image signals from tissues of a particular organ. A contrast agent which intensifies image signals from the MRI target is called a 'positive contrast agent' and one which weakens the signals relative to the surroundings is called a 'negative contrast agent'.

The contrast agents approved for use in human for MRI include ionic Gd(III) complexes such as diethylentriamine-N,N,N',N'',N''-pentaacetate and (N-Me-glucamine)$_2$[Gd (DTPA)(H$_2$O)] (Magnevist, Schering) exhibiting a magnetic relaxation rate of about 4.7 mM$^{-1}$s$^{-1}$ (20 MHz, 298 K) and neutral Gd(III) complexes such as [Gd(DTPA-bismethylamide)(H$_2$O)] (Omniscan, Nycomed) exhibiting a magnetic relaxation rate of about 4.4 mM$^{-1}$s$^{-1}$ (20 MHz, 298 K).

The properties required for the MRI contrast agent include thermodynamic stability, water solubility and multidentate structure that allows formation of paramagnetic Gd(III) ions, i.e. high water relaxivity. In addition, the MRI contrast agent should be chemically inert, have low cytotoxicity in vivo and be completely excreted after diagnostic examination.

However, the above contrast agents have relatively low water solubility and magnetic relaxation rate and is relatively highly cytotoxic in vivo. Accordingly, there is a strong need for the development of an optimized MRI contrast agent.

The inventors of the present invention have studied to solve the above-described problems. As a result, they have found that a gadolinium complex comprising a DO3A-tranexamic acid or its ester compound synthesized according to the present invention has bifunctionality of liver-specific and blood-pool contrasting effect and exhibits high relaxivity.

DISCLOSURE

Technical Problem

The present invention is directed to providing a DO3A-tranexamic acid or its ester compound, which has a structure of Chemical Formula 1.

The present invention is also directed to providing a composition for a ligand (L) of a complex comprising the compound and a gadolinium complex comprising the compound as a ligand.

The present invention is also directed to providing a magnetic resonance imaging (MRI) contrast agent comprising a gadolinium complex, which has high relaxivity and enhanced thermodynamic and kinetic stability.

Technical Solution

According to an aspect of the present invention, there is provided a DO3A-tranexamic acid or its ester compound, which is represented by the following Chemical Formula 1:

[Chemical Formula 1]

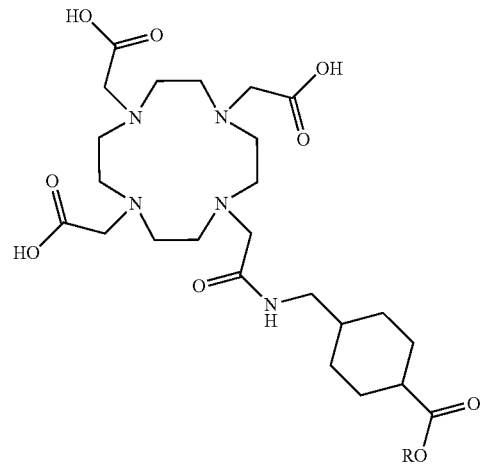

wherein R is selected from the group consisting of H, Me, Et, (CH$_2$)$_2$OH, CH$_2$OMe and CH$_2$CH=CH$_2$.

According to another aspect of the present invention, there is provided a method of preparing the DO3A-tranexamic acid or its ester compound, comprising:

a) adding bromoacetyl bromide to trans-4(aminomethyl) cyclohexaneethylcarboxylate hydrochloride with stirring;

b) adding DO3A-($^t$BuO)$_3$ to the mixture with stirring;

c) adding TFA to the mixture to deprotect a tert-butyl group;

d) conducting silica gel chromatography after removing all of solvent under low pressure and dissolving the mixture in methanol; and e) drying the product obtained from the chromatography under vacuum state to obtain a DO3A-tranexamic acid or its ester compound.

The preparation method according to the present invention is described in FIG. 1. Hereinafter, the present invention will be described in further detail.

The trans-4(aminomethyl)cyclohexaneethylcarboxylate hydrochloride (Compound 1b) in the step a) is synthesized using trans-4-(aminomethyl)cyclohexanecarboxylic acid. After the step a) is completed, ethyl 4-((2-bromoacetamido) methyl)cyclohexanecarboxylate (Compound 2b) is synthesized. After the step b) is completed, tert-butyl N,N',N''— (N'''-(2-((4-ethoxycarbonyl)cyclohexyl)methylamino-2-oxoethyl)-1,4,7,10-tetra azacyclododecane-1,4,7-triyl) triacetate (Compound 3b) is synthesized. After the step c) is completed, a DO3A-tranexamic acid ester derivative 1 is finally obtained through the steps d) and e).

The DO3A-tranexamic acid ester derivative 1 is one of Compound 4b shown in the scheme of FIG. 1.

In the method according to the present invention, allyl-trans-4(aminomethyl)cyclohexaneethylcarboxylate hydrochloride may be added instead of trans-4(aminomethyl)cyclohexaneethylcarboxylate hydrochloride in the step a).

The allyl-trans-4(aminomethyl)cyclohexaneethylcarboxylate hydrochloride may be synthesized fusing trans-4-(aminomethyl)cyclohexanecarboxylic acid (Compound 1c). After the step a) is completed using Compound 1c, allyl 4-((2-bromoacetamido)methyl)cyclohexanecarboxylate (Compound 2c) is synthesized. After the step b) is completed using Compound 2c, tert-butyl N,N',N''—(N'''-(2-((4-allyloxycarbonyl)cyclohexyl)methylamino-2-oxoethyl)-1,4,7,10-tetraazacyclododecane-1,4,7-triyl)triacetate (Compound 3c) is synthesized. After the step c) is completed, a DO3A-tranexamic acid ester derivative 2 is finally obtained through the steps d) and e).

The DO3A-tranexamic acid ester derivative 2 is one of Compound 4c shown in the scheme of FIG. 1.

Compound 4b, which is the DO3A-tranexamic acid ester derivative 1 synthesized above may be used prepare a DO3A-tranexamic acid (Compound 4a). Details will be described in the Examples section.

According to another aspect of the present invention, there is provided a composition for a ligand (L) of a complex, which comprises the DO3A-tranexamic acid or its ester compound according to the present invention.

As used herein the term "ligand (L)" means a chelate to which a metal atom can coordinately bonded.

According to another aspect of the present invention, there is provided a complex comprising the DO3A-tranexamic acid or its ester compound according to the present invention as a ligand (L) and a metal atom coordinately bonded to the ligand.

In the complex according to the present invention, the metal atom may be gadolinium (Gd).

In the complex according to the present invention, the complex may be represented by the Chemical Formula of $[Gd(L)(H_2O).xCH_3COOH.yH_2O]$.

The complex comprising the metal atom according to the present invention is prepared using the DO3A-tranexamic acid or its ester compound (Compounds 4a-4-c) synthesized as described above. Each of Compounds 4a-4-c is reacted with gadolinium chloride hexahydrate ($GdCl_3.6H_2O$) to prepare the gadolinium complex.

According to another aspect of the present invention, there is provided a magnetic resonance imaging (MRI) contrast agent which comprises the complex as an active ingredient.

The contrast agent according to the present invention has bifunctionality of liver-specific and blood-pool contrasting effect. In addition, the contrast agent has high relaxivity and enhanced thermodynamic and kinetic stability.

Specifically, as confirmed in the Examples section, the MRI contrast agent comprising the gadolinium complex (Compounds 5a, 5b and 5c) synthesized according to the present invention as an active ingredient exhibits high paramagnetic relaxation rate for 72 hours as measured by $R_1^P(t)/R_1^P(0)$ and exhibits good kinetic stability, retaining about 98% or more paramagnetic relaxation rate. These are nearly the same as those of Dotarem® which is currently marketed as a MRI contrast agent. In addition, when relaxation times ($T_1$, $T_2$) and relaxivities ($R_1$, $R_2$) of the gadolinium complex according to the present invention was compared with the commercially available contrast agent, it was confirmed that Compounds 5b and 5c have very high $R_1$ values. In particular, the $R_1$ value of Compound 5c was 2.6 times higher than that of Dotarem®. It is thought that such a high $R_1$ value is due to increased molecular weight as compared to Dotarem®. The increased molecular weight leads to increased rotational correlation time and thus to high $R_1$ relaxivity. Since a contrast agent having high relaxivity results in high contrast enhancement at relatively lower administration amount, the MRI contrast agent according to the present invention is expected to exhibit excellent contrast enhancement effect. Indeed, when contrasting effect was investigated using mice, administration of the MRI contrast agent according to the present invention resulted in enhanced contrasting effect in liver, heart and blood.

Advantageous Effects

A magnetic resonance imaging (MRI) contrast agent comprising a gadolinium complex prepared according to the present invention as an active ingredient has higher relaxivity as compared to the currently commercially available contrast agent. In addition, the MRI contrast agent according to the present invention has bifunctionality of liver-specific and blood-pool contrasting effect. Accordingly, since the MRI contrast agent comprising the gadolinium complex according to the present invention satisfies the key properties required for a contrast agent for MRI, it can be widely used as an MRI contrast agent and can provide enhanced contrasting effect as compared to the existing contrast agent.

MODE FOR INVENTION

Figure 1:
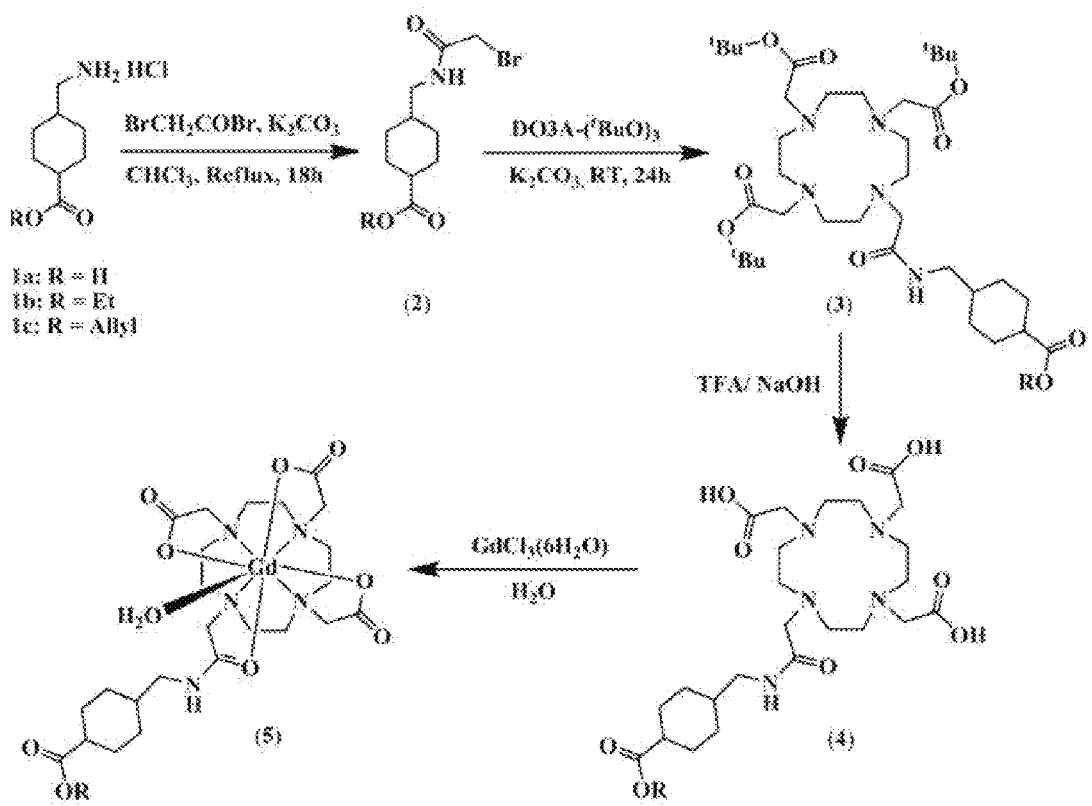
FIG. 1 describes a scheme for preparing a gadolinium complex according to the present invention.

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Preparation of DO3A Conjugates

DO3A conjugates were synthesized as follows and the synthesized compounds were identified by NMR. $^1H$ and $^{13}C$ NMR measurements were performed using a Bruker Advance 400 or 500 spectrometer (Korea Basic Science Institute). Chemical shifts were given as δ values with reference to tetramethylsilane (TMS) as an internal standard. Coupling constants are represented in Hz units.

1-1. Synthesis of DO3A-tranexamic Acid Ester Derivative 1

(1) Synthesis of trans-4-(aminomethyl)cyclohexaneethylcarboxylate hydrochloride (1b)

First, trans-4-(aminomethyl)cyclohexaneethylcarboxylate hydrochloride was synthesized using trans-4-(aminomethyl)cyclohexanecarboxylic acid purchased form TCI (Japan).

Trans-4-(aminomethyl)cyclohexanecarboxylic acid (1.57 g, 10 mmol) was added to 40 mL of ethanol at $0^2$C and stirred. After slowly adding thionyl chloride (0.9 mL, 12 mmol), the mixture was stirred for 10 min while keeping cold. Then, after refluxing at 70° C. for 1 h, the reaction mixture was cooled to room temperature. After completely removing the solvent under reduced pressure, the residue was washed twice with hexane (25 mL) to remove the remaining solvent. The mixture with the solvent completely removed was dried in dried under vacuum for 6 h to obtain trans-4-(aminomethyl)cyclohexaneethylcarboxylate hydrochloride. Yield was 2.13 g (96%).

$^1$H NMR ($d_6$-DMSO): δ=4.03 (q, J=7.08, 2H, OCH$_2$CH$_3$), 2.61 (m, 1H, H13), 2.21 (m, 1H, H10), 1.85 (m, 2H, H9), 1.27 (m, 4H, H12H11), 1.16 (t, J=7.06, 3H, OCH$_2$CH$_3$), 0.96 (m, 4H, H12H11). Anal. Calc. for $C_{10}H_{20}ClNO_2$: C, 54.17; H, 9.09; N, 6.32. Found: C, 53.78; H, 8.91; N, 6.34.

(2) Synthesis of Ethyl 4-((2-bromoacetamido)methyl)cyclohexanecarboxylate (2b)

To a mixture of trans-4-(aminomethyl)cyclohexaneethylcarboxylate hydrochloride (3.00 g, 13.5 mmol) prepared as above and K$_2$CO$_3$ (3.73 g, 27.1 mmol) in CH$_3$CN (100 mL) at 0° C. was added a solution of bromoacetyl bromide (1.1 mol equiv in 20 mL of CH$_3$CN) slowly over 1 h. After 18 h of stirring at 80° C., the inorganic salts were removed by filtration and the organic phase was evaporated under reduced pressure. The residue was washed with H$_2$O (30 mL×3 times) and dissolved in CH$_2$Cl$_2$. The organic phase was dried over Na$_2$SO$_4$, filtered, and evaporated to give a crude product which was further purified by chromatography on silica [gradient elution CH$_2$Cl$_2$ to 30% ethyl acetate (EA)-CH$_2$Cl$_2$, $R_f$=0.5 (EA/CH$_2$Cl$_2$=4:6)] to obtain ethyl 4-((2-bromoacetamido)methyl)cyclohexanecarboxylate as a white solid. Yield: 2.49 g (60%).

$^1$H NMR (CDCl$_3$): δ=6.54 (br, 1H, —CONH—), 4.12 (q, 2H, —OCH$_2$CH$_3$), 3.90 (s, 2H, BrCH$_2$CO—), 3.16 (t, 2H, —CONHCH$_2$—), 2.22 (m, 1H, CH$_3$CH$_2$COOCH—, cyclohexyl), 1.80-2.10 (m, 4H, CH$_2$—, cyclohexyl), 1.52 (m, 1H, NHCH$_2$CH—, cyclohexyl), 1.49-1.37 (m, 2H, —CH$_2$—, cyclohexyl), 1.24 (t, 3H, —COOCH$_2$CH$_3$), 1.08-0.92 (m, 2H, —CH$_2$—, cyclohexyl). $^{13}$CNMR (CDCl$_3$): δ=175.79 (BrCH$_2$CONH—), 165.57 (—COOCH$_2$CH$_3$), 60.23 (—COOCH$_2$CH$_3$), 45.96 (—COOCH—, cyclohexyl), 43.17 (—NHCH$_2$CH—), 37.12 (—NHCH$_2$CH—, cyclohexyl), 29.68 (BrCH$_2$CO—), 29.35 (—CH$_2$—, cyclohexyl), 28.34 (—CH$_2$—, cyclohexyl), 14.22 (—COOCH$_2$CH$_3$). Anal. Calc. for $C_{12}H_{20}BrNO_3$: C, 47.07; H, 6.58; N, 4.57. Found: C, 47.78; H, 6.85; N, 4.72 (purity>95%). FAB-MS (m/z): Calc. for $C_{12}H_{21}BrNO_3$, 306.07 ([MH]$^+$). Found: 306.20.

(3) Synthesis of DO3A-($^t$BuO)$_3$.HBr

To a stirred mixture of cyclen (1,4,7,10-tetraazacyclododecane) (Strem, USA) (5.34 g, 30 mmol) and NaHCO$_3$ (8.34 g, 99 mmol) in CH$_3$CN (120 mL) at 0° C. was added tert-butyl bromoacetate (19.35 g, 99 mmol) dropwise over 30 min. The reaction mixture was further stirred for 48 h at room temperature. Any inorganic solids were removed by filtration, and the solvent was removed from the filtrate to leave a solid. The solid was taken up in chloroform, and the solid suspension was removed by filtration. The filtrate was concentrated, and the resulting solid was recrystallized from toluene to obtain DO3A-($^t$BuO)$_3$.HBr as a white solid. Yield: 11.30 g (61%).

$^1$H NMR (CDCl$_3$): δ=3.37 (s, 4H, 2×CH$_2$ acetates), 3.29 (s, 2H, CH$_2$ unique acetate), 3.10 (br, 4H, —CH$_2$CH$_2$-ring), 2.88-2.93 (br m, 12H, —CH$_2$CH$_2$-ring), 1.55 (s, 27H, C(CH$_3$)$_3$). $^{13}$CNMR (CDCl$_3$): δ=28.19 (—C(CH$_3$)), 47.52 (—CH$_2$CH$_2$—, cyclic ring, asymmetric), 49.15 (—CH$_2$CH$_2$—, cyclic ring, asymmetric), 51.31 (—CH$_2$CH$_2$—, cyclic ring, symmetric), 58.17 (—CH$_2$COO—, acetate), 81.66 (—C(CH$_3$)), 169.62 (—CH$_2$COO—, unique acetate), 170.51 (—CH$_2$COO—, acetate). Anal. Calc. for $C_{26}H_{51}N_4O_6$.HBr: C, 52.43; H, 8.63; N, 9.41. Found: C, 52.10; H, 8.90; N, 9.00 (purity>95%). MALDI-TOF MS (m/z): Calc. for $C_{26}H_{51}N_4O_6$, 515.38 ([MH]$^+$). Found: 515.39.

(4) Synthesis of tert-butyl N,N',N"—(N'''-(2-((4-ethoxycarbonyl)cyclohexyl)methylamino-2-oxoethyl)-1,4,7,10-tetraazacyclododecane-1,4,7-triyl)triacetate (3b)

To a stirred solution of ethyl 4-((2-bromoacetamido)methyl)cyclohexanecarboxylate prepared as above (1.13 g, 3.69 mmol) in CH$_3$CN (10 mL) was added slowly a mixture of DO3A-(tBuO)$_3$.HBr (2 g, 3.36 mmol) and K$_2$CO$_3$ (1.40 g, 11.07 mmol) suspended in CH$_3$CN (50 mL). The mixture was stirred at room temperature for 24 h, after which any solids were removed by filtration. The filtrate was evaporated under reduced pressure to yield a yellowish white solid. The crude compound was purified by silica gel chromatography (gradient elution CH$_2$Cl$_2$ to 10% MeOH—CH$_2$Cl$_2$, $R_f$=0.5 (MeOH:CH$_2$Cl$_2$=1:9)) to give tert-butyl N,N',N"—(N'''-(2-((4-ethoxycarbonyl)cyclohexyl)methylamino-2-oxoethyl)-1,4,7,10-tetraazacyclododecane-1,4,7-triyl)triacetate as a white solid. Yield: 2.11 g (85%).

$^1$H NMR (CDCl$_3$): δ=4.11 (q, 2H, —COOCH$_2$CH$_3$), 3.38 (s, 4H, 2×CH$_2$ acetate), 3.29 (s, 2H, CH$_2$ unique acetate), 3.05-3.15 (br m, 6H, overapped-CH$_2$CH$_2$-ring and CH$_2$ acetate arm), 2.85-2.94 (br m, 12H, —CH$_2$CH$_2$-ring), 2.18-2.24 (m, 1H, CH$_3$CH$_2$COOCH—), 1.88-2.00 (m, 4H, —CH$_2$—, cyclohexyl), 1.60 (m, 1H, —NHCH$_2$CH—, cyclohexyl), 1.46 (s, 27H, —C(CH$_3$)$_3$), 1.41-1.45 (m, 2H, —CH$_2$—, cyclohexyl), 1.25 (t, 3H, —OCH$_2$CH$_3$), 1.01-1.05 (m, 2H, —CH$_2$—, cyclohexyl). FAB-MS (m/z): Calc. for $C_{38}H_{70}N_5O_9$, 740.52 ([MH]$^+$); $C_{38}H_{69}N_5O_9$Na, 762.50 ([MNa]$^+$). Found: 740.40 ([MH]$^+$), 762.40 ([MNa]$^+$). MALDI-TOF MS (m/z). Found: 740.50 ([MH]$^+$), 762.50 ([MNa]$^+$). Purity<90%.

(5) Synthesis of DO3A-tranexamic Acid Ester Derivative 1 (4b)

A solution of tert-butyl N,N',N"—(N'''-(2-((4-ethoxycarbonyl)cyclohexyl)methylamino-2-oxoethyl)-1,4,7,10-tetraazacyclododecane-1,4,7-triyl)triacetate (2.0 g, 2.70 mmol) prepared as above in TFA (10 mL) was stirred at room temperature for 24 h. The solution was then diluted with diethyl ether (50 mL), filtered, washed several times with diethyl ether, and dried under vacuum to obtain a white solid product.

The product was determined as $C_{26}H_{45}N_5O_9 \cdot CF_3COOH$ by acidimetric titration and elemental analysis. Yield: 2.25 g (91%).

$^1$H NMR (D$_2$O): δ=3.95-4.01 (q, 2H, —OCH$_2$CH$_3$), 3.62 (br s, 8H, acetatearm-CH$_2$—), 3.14 (br s, 16H, —CH$_2$CH$_2$-cyclic ring), 2.90-2.92 (d, 2H, —CONHCH$_2$—), 2.13-2.20 (m, 1H, CH$_3$CH$_2$COOCH—), 1.79-1.82 (m, 2H, —CH$_2$—, cyclohexyl), 1.62-1.65 (m, 2H, —CH$_2$—, cyclohexyl), 1.31-1.35 (m, 1H, —NHCH$_2$CH—, cyclohexyl), 1.19-1.27 (m, 2H, —NHCH$_2$CH—, cyclohexyl), 1.06-1.10 (t, 3H, —OCH$_2$CH$_3$), 0.79-0.89 (m, 2H, —CH$_2$—, cyclohexyl). $^{13}$CNMR (500 NMR, D$_2$O): δ=13.3 (—CH$_2$CH$_3$), 28.10 (—CH$_2$CH$_2$—, cyclohexyl), 29.10 (—CH$_2$CH$_2$—, cyclohexyl), 36.56 (—(CH$_2$)$_2$CHCH$_2$NH—, cyclohexyl), 43.16 (—(CH$_2$)$_2$CHCH$_2$NH—), 45.29 (—(CH$_2$)$_2$CHCOOCH$_2$CH$_3$), 49.12 (—CH$_2$CH$_2$—, cyclic ring, asymmetric), 50.25 (—CH$_2$CH$_2$—, cyclic ring, symmetric), 52.22 (—CH$_2$COONH—), 55.17 (—CH$_2$COOH, acetate), 171.01 (—CH$_2$CONH—), 179.32 (—CH$_2$COOCH$_2$CH$_3$), 181.36 (—CH$_2$COOH). Anal. Calc. for $C_{26}H_{45}N_5O_9 \cdot 3CF_3COOH$: C, 42.06; H, 5.29; N, 7.66. Found: C, 42.09; H, 5.85; N, 8.26 (Purity>95%). MALDI-TOF-MS (m/z): Calc. for $C_{26}H_{46}N_5O_9$, 572.33 ([MH]$^+$), $C_{26}H_{45}N_5O_9Na$, 594.31 ([MNa]$^+$). Found: 572.44 ([MH]$^+$), 594.44 ([MNa]$^+$).

1-2. Synthesis of DO3A-tranexamic Acid Ester Derivative 2

(1) Synthesis of allyl-trans-4-(aminomethyl)cyclohexaneethylcarboxylate hydrochloride (1c)

First, allyl-trans-4-(aminomethyl)cyclohexaneethylcarboxylate hydrochloride was synthesized using trans-4-(aminomethyl)cyclohexanecarboxylic acid purchased form TCI (Japan).

Trans-4-(aminomethyl)cyclohexanecarboxylic acid (3.93 g, 25 mmol) was added to 50 mL of allyl alcohol at 0° C. and stirred. After slowly adding thionyl chloride (3.57 g, 30 mmol), the mixture was stirred for 10 min while keeping cold. Then, after refluxing at 75° C. for 1 h, the reaction mixture was cooled to room temperature. After completely removing the solvent under reduced pressure, the residue was washed three times with hexane (30 mL) to remove the remaining solvent. The mixture with the solvent completely removed was dried in dried under vacuum for 6 h to obtain allyl-trans-4-(aminomethyl)cyclohexaneethylcarboxylate hydrochloride. Yield was 4.79 g (82%).

$^1$H NMR (d$_6$-DMSO, 400 MHz): δ=7.81 (br s, 3H, NH$_2$HCl), 5.71 (m, 1H), 5.16 (m, 2H, OCH$_2$CH=CH$_2$), 4.32 (m, 2H, OCH$_2$CH=CH$_2$), 2.40 (d, J=7.00, 2H, H9), 2.07 (m, 1H, H13), 1.66 (m, 4H, H11/H12), 1.33 (m, 1H, H10), 0.92 (m, 4H, H11/H12). $^{13}$C NMR (d$_6$-DMSO, 100 MHz): δ=174.77 (C1), 133.12 (OCH$_2$CH=CH$_2$), 117.78 (OCH$_2$CH=CH$_2$), 64.46 (OCH$_2$CH=CH$_2$), 44.01 (CH$_2$NH$_2$), 42.32 (C2), 35.12 (C4), 29.02 (C3, C5), 28.20 (C2, C6). Anal. Calc. for $C_{11}H_{19}NO_2 \cdot HCl$: C, 56.52; H, 8.62; N, 5.99. Found: C, 56.37; H, 8.54; N, 5.76%. FABMS (m/z): Calc. for $C_{11}H_{20}NO_2$, 198.28 ([MH]$^+$). Found: 198.10.

(2) Synthesis of Allyl 4-((2-bromoacetamido)methyl)cyclohexanecarboxylate (2c)

The title compound was prepared by the same procedure described as that in (2) of the above Example 1-1, except for replacing ethyl-trans-4(aminomethyl)cyclohexanecarboxylate hydrochloride with ally-trans-4-(aminomethyl) cyclohexanecarboxylate hydrochloride (3.02 g, 12.83 mmol). The product was obtained as a white solid. Yield: 2.86 g (70%).

$^1$H NMR (CDCl$_3$): δ=6.54 (br, 1H, —CONH—), 5.87-5.92 (m, 1H, —OCH$_2$CH=CH$_2$), 5.24-5.32 (m, 2H, —OCH$_2$CH=CH$_2$), 4.57 (d, 2H, —OCH$_2$CH=CH$_2$), 3.89 (s, 2H, BrCH$_2$CONH—), 3.16 (t, 2H, —CH$_2$NHCO—), 2.27 (m, 1H, CH$_2$=CHCH$_2$COOCH—), 1.82-2.03 (m, 4H, —CH$_2$—, cyclohexyl), 1.52 (m, 1H, —NHCH$_2$CH—), 1.46-1.51 (m, 2H, CH$_2$—, cyclohexyl), 0.92-1.10 (m, 2H, —CH$_2$—, cyclohexyl). $^{13}$CNMR (d$_6$-DMSO): δ=175.32 (BrCH$_2$CONH—), 165.33 (—COOCH$_2$CH=CH$_2$), 132.29 (—COOCH$_2$CH=CH$_2$), 118.01 (—COOCH$_2$CH=CH$_2$), 64.92 (—COOCH$_2$CH=CH$_2$), 45.98 (—COOCH—, cyclohexyl), 43.17 (—NHCH$_2$CH—), 37.12 (—NHCH$_2$CH—, cyclohexyl), 29.68 (BrCH$_2$CO—), 29.44 (—CH$_2$—, cyclohexyl), 28.35 (—CH$_2$—, cyclohexyl). Anal. Calc. for $C_{13}H_{20}BrNO_3$: C, 49.07; H, 6.34; N, 4.40. Found: C, 48.90; H, 6.39; N, 4.27 (purity>95%). FAB-MS (m/z): Calc. for $C_{13}H_{21}BrNO_3$, 318.07 ([MH]$^+$). Found: 318.30.

(3) Synthesis of tert-butyl N,N',N"—(N'''-(2-((4-allyloxycarbonyl)cyclohexyl)methylamino-2-oxoethyl)-1,4,7,10-tetraazacyclododecane-1,4,7-triyl)triacetate (3c)

The title compound was prepared by the same procedure as that in (4) of the above Example 1-1, except for replacing ethyl 4-((2-bromoacetamido)methyl)cyclohexanecarboxylate with allyl 4-((2-bromoacetamido)methyl)cyclohexanecarboxylate (1.17 g, 3.69 mmol). The product was obtained as a white solid. Yield: 2.10 g (83%).

$^1$H NMR (CDCl$_3$): δ=5.85-5.95 (m, 1H, —CH$_2$CH=CH$_2$), 5.19-5.31 (m, 2H, —CH$_2$CH=CH$_2$), 4.54 (d, 2H, —CH$_2$CH=CH$_2$), 0.95-1.05 (m, 2H, —CH$_2$—, cyclohexyl), 1.37-1.45 (m, 2H, —CH$_2$—, cyclohexyl), 1.46 (s, 27H, —C(CH$_3$)$_3$), 2.21-3.51 (br m, 27H, overapped-CH$_2$CH$_2$-cyclic ring (16H), —CH$_2$-acetate arms (8H), —NHCH$_2$CH-(2H), —NHCH$_2$CH-(1H)), 1.90-2.00 (br m, 4H, —CH$_2$—, cyclohexyl), 1.60 (m, 1H, —OOCCH$_2$CH—). MALDI-TOF MS (m/z) Calc. for $C_{39}H_{69}N_5O_9Na$: 774.50 ([MNa]$^+$), $C_{39}H_{69}N_5O_9K$: 790.47 ([MK]$^+$). Found: 774.58 ([MNa]$^+$), 790.60 ([MK]$^+$). Purity<90%.

(4) Synthesis of DO3A-tranexamic Acid Ester Derivative 2(4c)

The title compound was obtained by the same procedure as that in (5) of the above Example 1-1, except for replacing tert-butyl N,N',N"—(N'''-(2-((4-ethoxycarbonyl)cyclohexyl)methylamino-2-oxoethyl)-1,4,7,10-tetraazacyclododecane-1,4,7-triyl)triacetate with tert-butyl N,N',N"—(N'''-(2-((4-allyloxycarbonyl)cyclohexyl)methylamino-2-oxoethyl)-1,4,7,10-tetraazacyclododecane-1,4,7-triyl)triacetate (2.03 g, 2.70 mmol). The product was obtained as a white solid. Yield: 2.60 g (89%).

$^1$H NMR (D$_2$O): δ=5.84-5.94 (m, 1H, —OCH$_2$CH=CH$_2$), 5.18-5.28 (m, 2H, —OCH$_2$CH=CH$_2$), 4.53-4.55 (d, 2H, —OCH$_2$CH=CH$_2$), 3.61-3.72 (m, 8H, —CH$_2$-acetatearms), 3.14-3.27 (br m, 16H, —CH$_2$CH$_2$-cyclic ring), 2.98-2.99 (d, 2H, —CONHCH$_2$—), 2.27-2.34 (m, 1H, CH$_3$CH$_2$COOCH—, cyclohexyl), 1.91-1.93 (m, 2H, —CH$_2$—, cyclohexyl), 1.72-1.74 (m, 2H, —CH$_2$—, cyclohexyl), 1.40-1.48 (m, 1H, —NHCH$_2$CH—, cyclohexyl), 1.28-1.37 (m, 2H, —CH$_2$—, cyclohexyl), 0.88-0.98 (m, 2H, —CH$_2$—, cyclohexyl). $^{13}$CNMR (500 NMR, D$_2$O): δ=28.09 (—CH$_2$CH$_2$—, cyclohexyl), 29.05 (—CH$_2$CH$_2$—, cyclohexyl), 36.51 (—(CH$_2$)$_2$CHCH$_2$NH—, cyclohexyl), 43.06 (—(CH$_2$)$_2$CHCH$_2$NH—), 45.35 (—(CH$_2$)$_2$CHCOOCH$_2$CH=CH$_2$), 49.52 (—CH$_2$CH$_2$—, cyclic ring), 52.21 (—CH$_2$COONH—), 55.12 (—CH$_2$COOH, acetate), 65.58 (—COOCH$_2$CH=CH$_2$), 118.03 (—COOCH$_2$CH=CH$_2$), 132.06 (—COOCH$_2$CH=CH$_2$), 171.99 (—CH$_2$CONH—), 179.73 (—CH$_2$COOCH$_2$CH=CH$_2$), 181.28 (—CH$_2$COOH). Anal. Calc. for C$_{27}$H$_{45}$N$_5$O$_9$.2.4CF$_3$COOH: C, 43.76; H, 5.65; N, 8.28. Found: C, 43.65; H, 6.03; N, 9.07 (Purity>95%). MALDI-TOF MS (m/z): Calc. for C$_{27}$H$_{46}$N$_5$O$_9$, 584.33 ([MH]$^+$), C$_{27}$H$_{45}$N$_5$O$_9$Na, 606.31 ([MNa]$^+$). Found: 584.36 ([MH]$^+$), 606.32 ([MNa]$^+$).

1-3. Synthesis of DO3A-tranexamic acid (4a)

DO3A-tranexamic acid was synthesized using DO3A-tranexamic acid ester derivative 1 prepared as above.

To a solution of Compound 4b (1.0 g, 1.0 mmol) prepared in the above Example 1-1 in EtOH (20 mL) was added 5 N NaOH until the pH rose to 10. The solvent was then removed under reduced pressure and the resulting residue was taken up in methanol (10 mL). The solution was passed through a short column of silica gel (60 mesh) chromatography with methanol as an eluent. The residue obtained after removal of the solvent was triturated with diethyl ether and dried in vacuum to leave DO3A-tranexamic acid as a white solid. Yield: 0.50 g (85%).

$^1$H NMR (D$_2$O): δ=0.85-0.94 (m, 2H, —CH$_2$—, cyclohexyl), 1.20-1.29 (m, 2H, —CH$_2$—, cyclohexyl), 1.41 (br s, 1H, —NHCH$_2$CH—, cyclohexyl), 1.68-1.71 (m, 2H, —CH$_2$—, cyclohexyl), 1.80-1.83 (m, 2H, —CH$_2$—, cyclohexyl), 1.98-2.04 (m, 1H, HOOCCH—, cyclohexyl), 2.35-3.45 (br m, 26H, overapped-CH$_2$CH$_2$-cyclic ring (16H), —CH$_2$-acetate arms (8H), —CONHCH$_2$-(2H). $^{13}$CNMR (D$_2$O): δ=29.02 (—CH$_2$CH$_2$—, cyclohexyl), 29.74 (—CH$_2$CH$_2$—, cyclohexyl), 37.10 (—(CH$_2$)$_2$CHCH$_2$NH—, cyclohexyl), 44.80 (—(CH$_2$)$_2$CHCH$_2$NH—), 45.63 (—(CH$_2$)$_2$CHCOOH), 48.67 (—CH$_2$CH$_2$—, cyclic ring, symmetric), 51.56 (—CH$_2$CH$_2$—, cyclic ring, asymmetric), 52.06 (—CH$_2$CH$_2$—, cyclic ring, asymmetric), 55.51 (—CH$_2$COONH—), 55.80 (—CH$_2$COOH, unique acetate), 57.12 (—CH$_2$COOH, acetates), 170.84 (—CH$_2$CONH—), 171.92 (—CH$_2$COOH, unique), 177.02 (—CH$_2$COOH), 183.70 (—(CH$_2$)$_2$CHCOOH). MALDI-TOF MS (m/z): Calc. for C$_{24}$H$_{42}$N$_5$O$_9$, 544.30 ([MH]$^+$), C$_{24}$H$_{41}$N$_5$O$_9$Na, 566.28 ([MNa]$^+$). Found: 544.35 ([MH]$^+$), 566.33 ([MNa]$^+$). Purity<90%.

EXAMPLE 2

Preparation of Gadolinium Complexes

Gadolinium complexes were prepared using the DO3A conjugates synthesized in Example 1. The process for synthesizing the gadolinium complexes is described in detail below and each of the synthesized compounds was identified by FAB-Mass. FAB-Mass spectra were obtained using a JMS-700 mass spectrophotometer (JEOL, Japan).

2-1. Synthesis of Gadolinium Complex 1 (5a)

To a solution of DO3A-tranexamic acid (4a) (0.5 g, 0.9 mmol) prepared as above in deionized water (10 mL) was added gadolinium chloride hexahydrate (GdCl$_3$6H$_2$O; 0.34 g, 0.92 mmol), and the contents were stirred at room temperature for 18 h. After stirring, the reaction mixture was passed through Sephadex G-25 to remove free Gd ions from the product solution. The product was taken up in EtOH at 0° C., to which was added dropwise diethyl ether to obtain a gadolinium complex as a white solid. The absence of free Gd$^{3+}$ ions from the final product was checked with an orange indicator xylenol. Yield 0.71 g (90%).

Anal. Calc. for NaC$_{24}$H$_{37}$GdN$_5$O$_9$.CF$_3$COOH.H$_2$O: C, 36.66; H, 4.73; N, 8.22. Found: C, 36.86; H, 4.97; N, 7.50 (Purity>95%). FAB-MS (m/z): Calc. for C$_{24}$H$_{38}$GdN$_5$O$_9$Na, 721.18 ([MNa(H$_2$O)]$^+$). Found: 721.19. HR-FABMS (m/z): Calc. for C$_{24}$H$_{39}$GdN$_5$O$_9$, 699.1989 ([MH-(H$_2$O)]$^+$). Found: 699.1984.

2-2. Synthesis of Gadolinium Complex 2 (5b)

The title compound was obtained by the same procedure as that for 5a in the above Example 2-1, except for replacing DO3A-tranexamic acid (4a) with DO3A-tranexamic acid ester derivative 1 (4b) (0.913 g, 1 mmol). Yield: 1.12 g (95%).

Anal. Calc. for C$_{26}$H$_{44}$GdN$_5$O$_{10}$.2.5CF$_3$COOH.8H$_2$O: C, 31.74; H, 5.37; N, 5.97. Found: C, 31.51; H, 5.02; N, 6.01 (Purity>95%). HR-FABMS (m/z): Calc. for C$_{26}$H$_{42}$GdN$_5$O$_9$Na, 749.2128 ([MNa—(H$_2$O)]$^+$). Found: 749.2126.

2-3. Synthesis of Gadolinium Complex 3 (5c)

The title compound was obtained essentially by the same procedure as that for 5a in the above Example 2-1, except for replacing DO3A-tranexamic acid (4a) with DO3A-tranexamic acid ester derivative 2 (4c) (0.857 g, 1 mmol). Yield 1.01 g (90%).

Anal. Calc. for C$_{27}$H$_{44}$GdN$_5$O$_{10}$.2CF$_3$COOH.8H$_2$O: C, 33.01; H, 5.54; N, 6.21. Found: C, 32.69; H, 5.22; N, 6.70 (Purity>95%). HR-FABMS (m/z): Calc. for C$_{27}$H$_{43}$GdN$_5$O$_9$, 739.2308 ([MH-(H$_2$O)]$^+$). Found: 739.2307.

EXAMPLE 3

Measurement of Protonation Constants, Stability Constants, Selectivity Constants, Conditional Stability Constants and pM Values Protonation constants, stability constants, selectivity constants, conditional stability constants and pM values of the DO3A conjugates and gadolinium complexes prepared above were measured. Protonation constants ($K_i^H$) of the DO3A conjugates (4a-4-c) and stability constants of the gadolinium complexes (5a-5c) are defined in Equations 1 and 2, respectively, where H$_i$L (L=4; I=1, 2, . . . ) is the protonated ligand, L is the totally deprotonated free ligand, M is the unhydrolyzed aqua metal ion (Gd, Ca, Zn, Cu) and ML is the non-protonated and unhydrolyzed complex.

$$K_i^H = [H_iL]/[H_{i-1}L][H^+] \qquad \text{<Equation 1>}$$

$$K_{ML(therm)} = [ML]/[M][L] \qquad \text{<Equation 2>}$$

The protonation constants of the DO3A conjugates and the stability constants of their gadolinium (Gd(III)), calcium (Ca(II)), zinc (Zn(II)) and copper (Cu(II)) complexes were determined by potentiometric titration and the result is shown in Table 1. DOTA and acyclic analogues such as DTPA, EOB-DTPA, BOTPA and DTPA-BMA were used for comparison.

As seen from Table 1, the DO3A conjugates 4a-4c exhibit protonation constants (log $K_i^H$) and overall basicity (ΣpK$_a$) values that are comparable to or better than for their acyclic, open-chain counterparts. The overall basicity is directly correlated with the intensity of electrostatic interaction between the metal and the donor atoms of the ligand and thus with the stability of the chelate. Higher basicity of the ligand will surely lead to the formation of a thermodynamically more stable complex, which is demonstrated with the gadolinium complexes prepared from the respective DO3A conjugates.

Among the DO3A conjugates, 4a shows the highest log $K_{GdL}$ value (18.73), which is even higher than that of DOTA (18.33). This means that the Gd-ligand (L) complex stability is greater than that of DOTA under physiological conditions. The high complex stability achieved with 4a may be explained in terms of a stronger electrostatic interaction with the Gd(III) ion compared with 4b and 4c, with $L^{4-} \leftrightarrow Gd^{3+}$ and $L^{3-} \leftrightarrow Gd^{3+}$, respectively.

The pM value (which is indicative of binding between the ligand and the metal) reflects the influence of ligand basicity and protonation of the complex. Thus, the larger the pM value, the higher is the affinity of the ligand for the metal ion under the given condition. Table 1 shows that 4a-4-c exhibit higher pM values with gadolinium (Gd(III)) than with calcium (Ca(II)), zinc (Zn(II)) or copper (Cu(II)), indicating that the Gd(III) complexes of the DO3A conjugates are stable enough to avoid any interference by other endogenous metal ions.

(roughly log 10 orders of magnitude lower than Gd). Only the manganese ion is present in relatively high concentrations (55-125 mol/L) in the blood enough to replace the gadolinium ion and its association constant toward DTPA and DOTA is only about 4 orders of magnitude lower than that of gadolinium. Accordingly, the stability of Gd-complexes in the presence of the manganese ion is an important issue because transmetalation will induce release of free gadolinium ions into the body and possible elimination of the endogenous ion by the kidneys.

If transmetalation of a paramagnetic gadolinium complex by manganese ions were to occur in a phosphate-buffered solution, the free gadolinium ions would form $GdPO_4$, the solubility of which is very low ($K_{sp}=10^{-22.2}$ $mol^2/L^2$) and whose influence on the proton relaxation rate of water is negligible. The relative value of $R_1^P$ at time t, $R_1^P(t)/R_1^P(0)$, is therefore a good estimate of the extent of transmetalation. The evolution of $R_1^P(t)/R_1^P(0)$ over time gives relevant information about the kinetics of the reaction, whereas the plateau value theoretically reached at t=∞ will reflect the thermodynamic aspect.

Accordingly, in order to investigate the transmetalation kinetics of the gadolinium complexes according to the present

TABLE 1

Protonation constants, stability constants, selectivity constants, conditional stability constants and pM values

| | LogK (25° C., μ = 0.10M (KCl)) | | | | | | | |
|---|---|---|---|---|---|---|---|---|
| | 4a | 4b | 4c | DOTA[b] | DTPA[c] | EOB-DTPA[d] | BOPTA[e] | DTPA-BMA[f] |
| [HL]/[L][H] | 11.73 | 10.80 | 10.62 | 12.09 | 10.49 | 10.91 | 10.71 | 9.37 |
| [H₂L]/[HL][H] | 8.91 | 9.35 | 8.64 | 9.68 | 8.60 | 8.63 | 8.21 | 4.38 |
| [H₃L]/[H₂L][H] | 4.93 | 5.24 | 5.45 | 4.55 | 4.28 | 4.26 | 4.35 | 3.31 |
| [H₄L]/[H₃L][H] | 4.87 | — | — | 4.13 | 2.64 | 2.73 | 2.83 | — |
| ΣpK$_a$ | 30.43 | 25.39 | 25.72 | 30.45 | 26.01 | 26.53 | 26.10 | 17.06 |
| [GdL]/[Gd][L] | 24.58 | 22.07 | 21.52 | 25.30 | 22.46 | 23.46 | 22.6 | 16.85 |
| {logK$_{GdL}$(pH7.4)} | 18.73 | 16.72 | 16.99 | 18.33 | 18.14 | 18.7 | 18.4 | 14.84 |
| [CaL]/[Ca][L] | 14.01 | 15.42 | 14.97 | 17.23 | 10.75 | — | — | 7.17 |
| {logK$_{CaL}$(pH7.4)} | 8.16 | 10.06 | 10.44 | 10.26 | 6.43 | — | — | 5.11 |
| [ZnL]/[Zn][L] | 16.71 | 16.65 | 17.61 | 21.05 | 18.70 | — | — | 12.04 |
| {logK$_{ZnL}$(pH7.4)} | 10.86 | 11.29 | 13.08 | 14.08 | 14.38 | — | 13.9 | 10.02 |
| [CuL]/[Cu][L] | 17.56 | 17.39 | 19.30 | 22.63 | 21.38 | — | — | 13.03 |
| {logK$_{CuL}$(PH7.4)} | 11.70 | 12.04 | 14.77 | 15.66 | 17.06 | — | 17.3 | 11.06 |
| [logK$_{sel}$(Gd/Ca)] | 10.56 | 6.65 | 6.55 | 8.07 | 11.71 | — | — | 9.68 |
| [logK$_{sel}$(Gd/Zn)] | 7.87 | 5.43 | 3.91 | 4.25 | 3.76 | — | — | 4.81 |
| [logK$_{sel}$(Gd/Cu)] | 7.02 | 4.68 | 2.21 | 2.67 | 1.08 | — | — | 3.82 |
| pGd | 17.73 | 15.72 | 15.99 | 19.2 | 17.14 | — | — | 13.88 |
| pCa | 7.16 | 9.06 | 9.43 | — | 5.45 | — | — | 4.19 |
| pZn | 9.86 | 10.29 | 12.08 | 15.19 | 13.39 | — | — | 9.06 |
| pCu | 10.70 | 11.04 | 13.77 | 14.05 | 16.06 | — | — | 10.05 |

[a]pM = −log[M$^{n+}$]$_{free}$ at pH7.4; [M$^{n+}$]$_{total}$ = 1 μmol/dm³; [L]$_{total}$ = 1.1 μmol/dm³.
[b]Data obtained from ref. 1, 2.
[c]Data obtained from ref. 3.
[d]Data obtained from ref. 4, 5.
[e]Data obtained from ref. 6, 5.
[f]Data obtained from ref. 7.

EXAMPLE 4

Transmetalation Kinetics

Gd-chelates, although they are thermodynamically stable, may be kinetically labile enough to undergo transmetalation by endogenous ions. In such a process, the paramagnetic gadolinium (Gd(III)) ion is expelled from the complex. Endogenous ions likely to compete with gadolinium include copper, calcium and manganese. The copper ion is present in very low concentrations (1-10 μmol/L) in the blood and the calcium ion has relatively low affinity for DTPA or DOTA invention, the evolution of water proton relaxation rate ($R_1^P$) of a phosphate-buffered solution (pH 7.4) containing 2.5 mmol/L of Gd-complex and 2.5 mmol/L of $ZnCl_2$ with time was measured. To measure the change in the relaxation rate, 10 μL of a $ZnCl_2$ solution (250 mmol/L) was added to 1 mL of a buffered solution of the Gd-complex and the mixture was vigorously stirred. The same experiment was performed with Dotarem®, Omniscan®, Multihance®, Primovist® and ethyl tranexamate (6) with zinc acetate for comparison. The measurement was made on a 3T whole body system (Magnetom Tim Trip; Simens, Germany) at room temperature. The result is shown in FIG. 2.

Figure 2:
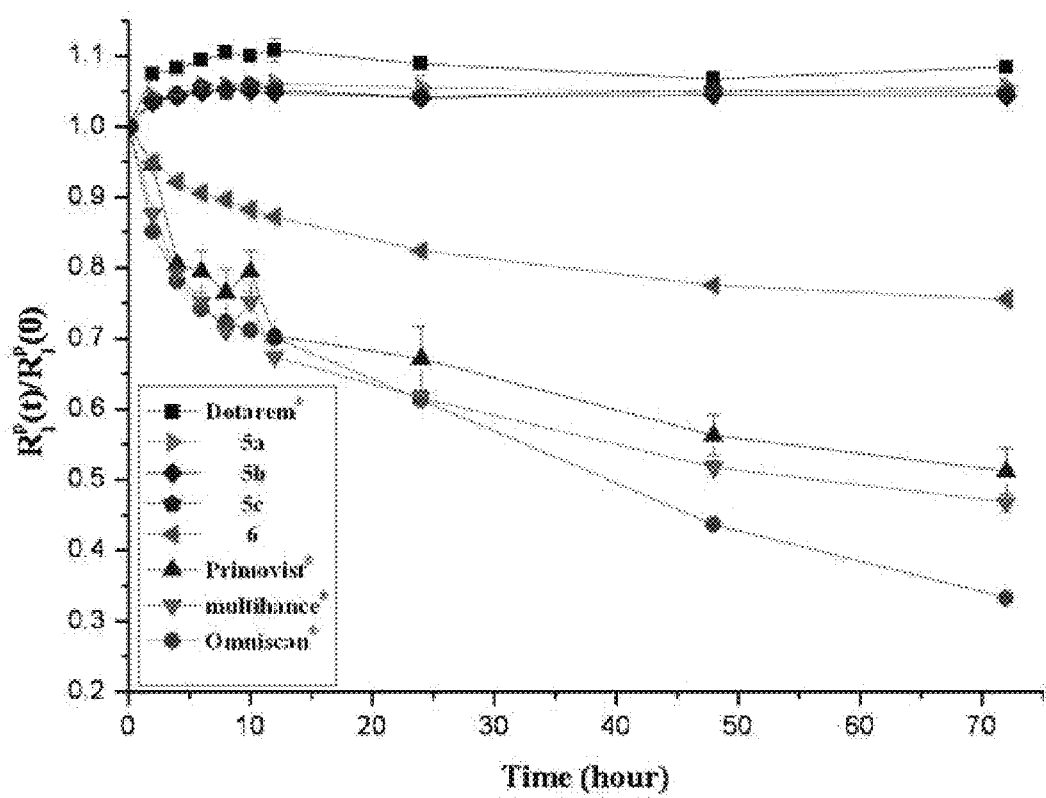
FIG. 2 shows a result of measuring change in paramagnetic relaxation rate ($R_1^P(t)/R_1^P(0)$) of gadolinium complexes according to the present invention (Compounds 5a-5c) and a commercially available MRI contrast agent.

FIG. 2 shows the evolution of the paramagnetic relaxation rate ($R_1^P(t)/R_1^P(0)$). As seen from FIG. 2, the complexes can be grouped into two depending on the pattern of evolution: (A) those adopting macrocyclic chelates such as Dotarem® and Compounds 5a-5c; and (B) those with acyclic chelates. The gadolinium complexes 1-3 (5a, 5b and 5c) synthesized according to the present invention possess pretty high kinetic stability (about 98% or higher) for 72 hours. These features are almost similar to that of Dotarem® and are thought to derive from structural similarity. That is, the gadolinium complexes have five-membered rings and the same macrocyclic motifs. The initial increase in the relaxation rate during the first 5 min may be due to the transient and better accessibility of gadolinium to water during the decomplexation process. On the other hand, Omniscan®, Multihance® and Primovist® exhibit a drastic decrease in the rate, which is expected judging from the fact that they adopt the acyclic, open-chain DTPA-bis(amide) motif. In particular, Omniscan® retains only 30% of the initial relaxation rate during the same period of time. The ethyl tranexamate (6) lies midway between the two (macrocyclic and acyclic) groups. This observation suggests that the tranexamic moiety in DTPA-bis(amide) should play a key role not only in thermodynamic stability but also in transmetalation kinetics. In this regard, the presence of the tranexamic moiety helps to enhance $R_1$ relaxivity through increase in the rotational correlation time as compared to DTPA-BMA.

EXAMPLE 5

Relaxation Times and Relaxivities

The relaxation times ($T_1$, $T_2$) and the relaxivities ($R_1$, $R_2$) of the gadolinium complexes prepared as above were measured. Contrast agents having higher relaxivity represent higher contrast enhancing effect with relatively smaller amounts.

Figure 3:
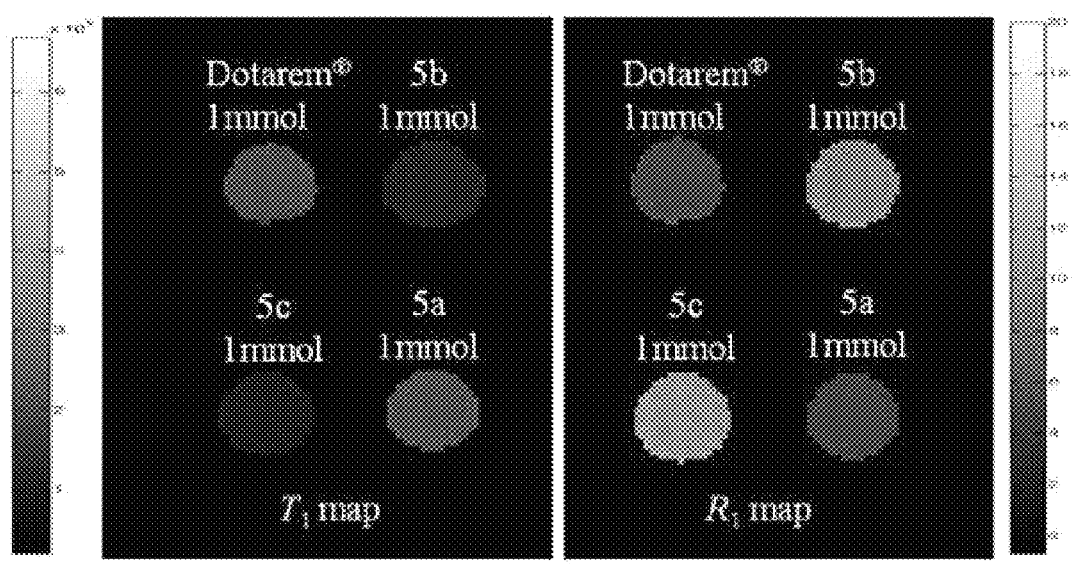
FIG. 3 shows relaxation time and relaxivity maps of gadolinium complexes according to the present invention (Compounds 5a-5c) and Dotarem®.

T1 measurements were carried out using an inversion recovery method with a variable inversion time (TI) at 1.5 T. The MR images were acquired at 35 different TI values ranging from 50 to 1750 ms. T1 relaxation times were obtained from the nonlinear least-squares fit of the signal intensity measured at each T1 value. For T2 measurements the CPMG (Carr-Purcell-Meiboon-Gill) pulse sequence was adapted for multiple spin-echo measurements. Thirty-four images were acquired with 34 different echo time (TE) values. T2 relaxation times were obtained from the nonlinear least-squares fit of the mean pixel values for the multiple spin-echo measurements at each echo time. Relaxivities were then calculated as an inverse (R=1/s·mM) of relaxation time per mM. The determined relaxation times and relaxivities are finally transformed to a phantom map. The phantom images were obtained with the same concentration of Dotarem® and gadolinium complexes or comparative purposes. The results were shown in FIG. 3 and Table 2. FIG. 3 shows the relaxation time and relaxivity maps on the gadolinium complexes (5a-c) of the present invention and Dotarem®. Table 2 summarizes the relaxation times and relaxivities for gadolinium complexes of the present invention along with other Gd-complexes.

Table 3 shows that Compounds 5b and 5c exhibit significantly higher R1 values than any of the clinically used contrast agents, especially the highest R1 reaching with 5c up to 2.6 times as high as that of Dotarem®. Such high values with the present system may be explained in part in terms of increased molecular weight as compared with Dotarem®. Such a molecular weight increase may increase the rotational correlation time, which in turn enhances relaxivity. An additional contribution to the enhanced relaxivity may come from some cooperative interaction between the inner-sphere water molecule and the carboxylic groups of the tranexamic moiety. For instance, the rate of water exchange in 5b and 5c seems to be enhanced by the presence of hydrophobic alkyl ester group. In contrast, however, the presence of hydrophilic group such as carboxylic acid in 5a would retard such an exchange with the inner-sphere water through hydrogen bonding, thereby lowering relaxivity.

TABLE 2

Relaxation times and relaxivities of gadolinium complexes

| Gadolinium complexes | $T_1$ (msec) | $R_1$ ($mM^{-1}sec^{-1}$) | $T_2$ (msec) | $R_2$ ($mM^{-1}sec^{-1}$) |
|---|---|---|---|---|
| 5a | 256.43 ± 2.63[a] | 3.9 ± 0.04 | 250.02 ± 2.50 | 4.0 ± 0.04 |
| 5b | 116.29 ± 1.35 | 8.6 ± 0.10 | 108.75 ± 2.60 | 9.2 ± 0.22 |
| 5c | 105.28 ± 1.33 | 9.5 ± 0.12 | 91.74 ± 0.25 | 10.9 ± 0.03 |
| Primovist ®[b] | 213.15 ± 9.07 | 4.7 ± 0.2 | 198.83 ± 23.4 | 5.1 ± 0.6 |
| Multihance ®[b] | 250.62 ± 12.5 | 4.0 ± 0.2 | 235 ± 27.4 | 4.3 ± 0.5 |
| Dotarem ® | 270.30 ± 2.92 | 3.7 ± 0.04 | 244.54 ± 12.5 | 4.1 ± 0.21 |
| Omniscan ®[c] | 209.8 ± 5.82 | 4.9 ± 0.14 | 290.9 ± 21.02 | 3.4 ± 0.25 |
| Water[c] | 842.5 ± 46.38 | 1.1 ± 0.06 | 1220 ± 167.20 | 0.82 ± 0.12 |

[a]Each value is presented as a mean value(±SD).
[b]Reference obtained from ref. 8.
[c]Reference obtained from ref. 9.

EXAMPLE 6

In Vivo MRI Test

To study the contrasting effect of the MRI contrast agent according to the present invention, six-week-old male ICR mice (weight=29-31 g) were used for the in vivo study. The mice were anesthetized by 1.5% isoflurane in oxygen and treated with gadolinium complex (5c) of the present invention at amount of 0.1 mmol of Gd/kg. After the treatment, the mouse was revived from anesthesia and placed in the cage with free access to food and water. The animals were maintained at approximately 37° C. using a warm water blanket.

MR images were taken with 1.5 T (GE Healthcare, Milwaukee, Wis., USA) equipped with a homemade small animal RF coil. The coil was of the receiver type with its inner diameter being 50 mm. The imaging parameters for 3D fast SPGR (spoiled GRASS images) are as follows: repetition time (TR)=8.8 ms; echo time (TE)=3.9 ms; 10 mm field of view (FOV); 256×192 matrix size; 1.0 mm slice thickness; number of acquisition (NEX)=4. The imaging parameters for spin-echo are as follows: TR=500 ms; TE=13 ms; 6 mm FOV; 192×128 matrix size; 1.5 mm slice thickness; NEX=4. Each image was taken with an interval of 3 min and 16 s. MR images were obtained for 26 h after injection of gadolinium complex (0.1 mmol/kg of 5c). For analysis of the obtained MR images, signal intensities in specific regions of interest (ROI) were measured using Advantage Window software (GE Medical, USA). The CNR was calculated using Equation 3, where SNR is the signal-to-noise ratio.

$$CNR=SNR_{post}-SNR_{pre}$$ <Equation 3>

The result is shown in FIGS. 4a-4c and 5.

Figure 4A:
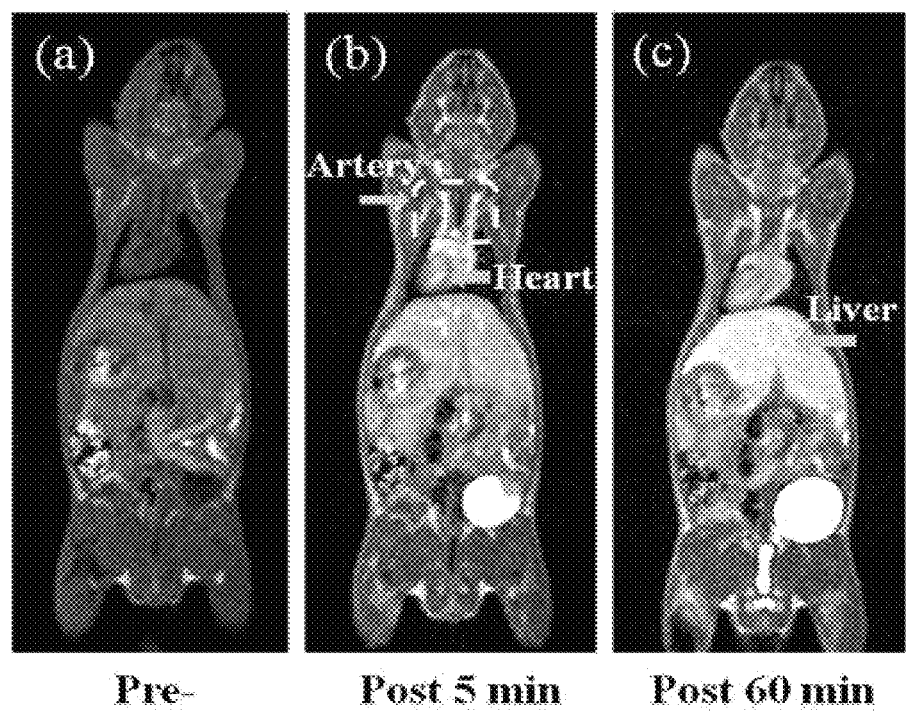
FIGS. 4a-4c show MR images of mice taken after injection of a gadolinium complex according to the present invention.
Figure 4B:
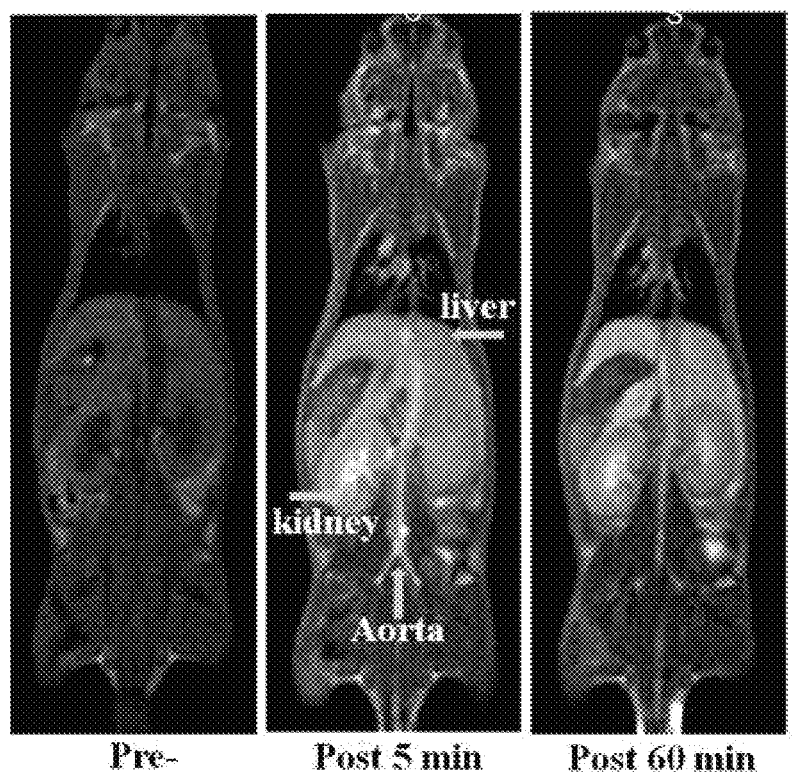
Figure 4C:
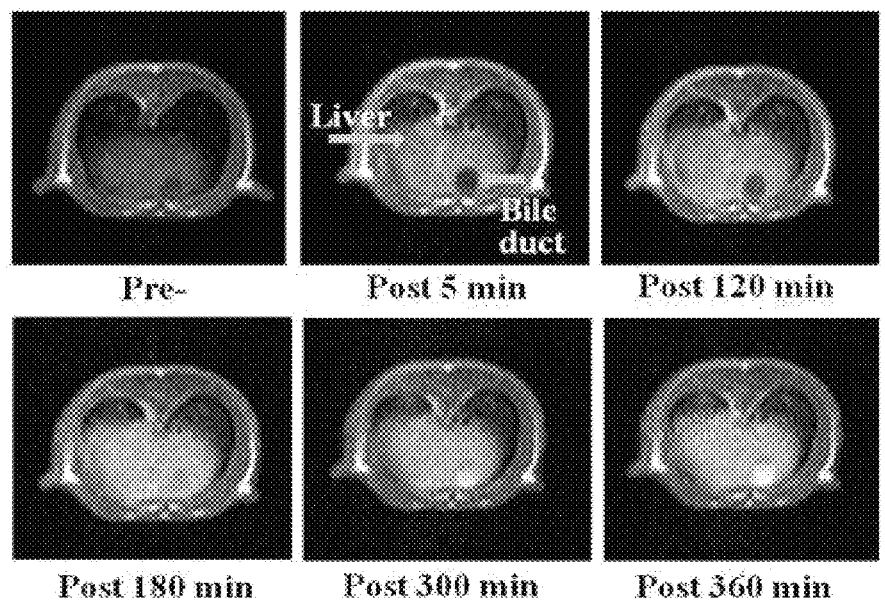

FIGS. 4a-4c show MR images. As seen from FIG. 4a, a strong signal is observed in the liver 1 h after the treatment with the gadolinium complex. Also, blood-pool effect is observed in the heart and the artery 1 h after the injection. And, as seen from FIG. 4b, enhanced contrasting effect is observed both in the kidney and the aorta 5 min after the treatment. Accordingly, it can be seen that the gadolinium complex according to the present invention exhibits bifunctional contrasting effect not only in the liver but also in the heart and artery.

FIG. 4c shows excretion pattern via the bile duct. Initially, a dark image was obtained because there was no contrast agent in the bile duct. However, after the contrast agent was injected, it is observed that the contrast agent was excreted slowly to the intestine via the bile duct through hepatobiliary uptake. This confirms that the contrast agent (5c) enhances contrast of the liver and then is excreted.

The excretion via the bile duct was further confirmed by measuring the concentration of Gd(III) ions with time through inductively coupled plasma (ICP) measurement. As a result, the concentration of Gd(III) ions in the liver and the kidneys decreased with time, as shown in Table 3. At 6 h after the injection, the Gd(III) ions were detected in the intestine, confirming that they are excreted via the liver and the bile duct.

TABLE 3

| ICP measurement result | | | | | |
|---|---|---|---|---|---|
| Organ | 1 h | 6 h | 24 h | 48 h | 72 h |
| Liver | 62.09 | 50.90 | 33.73 | 35.90 | 6.22 |
| Kidney | 65.17 | 68.22 | 10.89 | 6.91 | BD |
| Bile duct | BD | 13.95 | BD | BD | BD |
| Blood | 5.16 | 0.12 | BD | BD | BD |
| Intestine | BD | 2.485 | BD | BD | BD |

BD = below detection

The bifunctional contrasting effect of the gadolinium complex according to the present invention is due to the structural uniqueness of the gadolinium complex. Unlike the commercially available contrast agents, the macrocyclic chelate DO3A is used instead of acyclic DTPA. In particular, a contrast agent carrying an aromatic substituent on the chelate backbone has never been reported. It is considered that the blood-pool enhancement is a result of the lipophilic interaction between the aromatic substituent with organs or blood cells. In contrast, the commercially available Multihance® and Primovist® adopt acyclic DTPA moieties and their backbones are derivatized by aromatic resides in the expectation that their presence would increase noncovalent lipophilic interaction of the MRI contrast agents with organs or blood cells. Therefore, it can be seen that the presence of aromatics may not be an essential prerequisite for such a noncovalent lipophilic interaction of MRI contrast agents with organs or blood cells.

Figure 5:
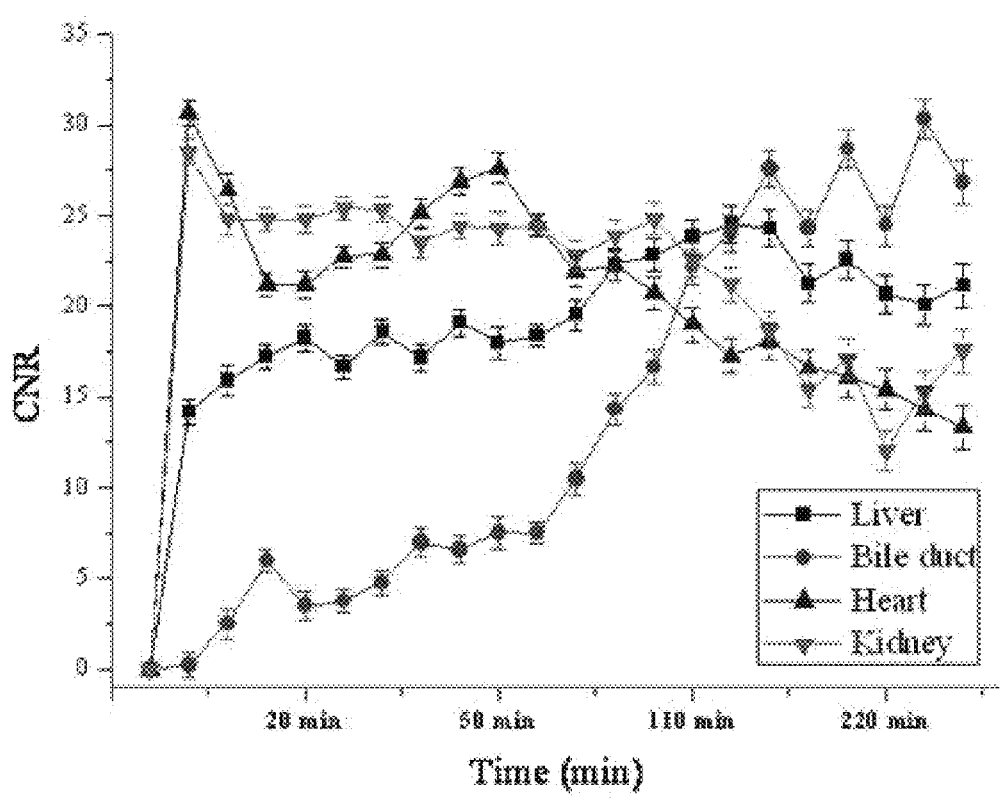
FIG. 5 shows profiles calculated from the MR images.

FIG. 5 shows contrast-to-noise ratio (CNR) profiles of the MR images. As seen from the figure, strongly enhanced hepatoceullar uptake is observed because of slow excretion of the injected MRI contrast agent through the bile duct. Such an excretion behavior may be explained in terms of longer circulation time of the MRI contrast agent.

EXAMPLE 7

Cell Viability

Cell viability of HEK-293 human embryonic kidney cells was measured by MTT assay.

First, HEK-293 cells were seeded onto a 96-well plate at a density of $1\times10^4$ cells/well using Dulbecco's modified Eagle's medium (DMEM; Gibco) supplemented with heat-inactivated FCS (10%), penicillin (100 IU/mL), streptomycin (100 mg/mL) and gentamicin (200 mg/mL) and incubated at 37° C. in a 5% $CO_2$ environment. After incubation for a day, the medium was replaced with DMEM containing the gadolinium complex (5a-5c) of the present invention (gadolinium concentration=0.01-1.0 mM), penicillin (100 IU/mL), streptomycin (100 mg/mL) and gentamicin (200 mg/mL). After further incubation for 24 h, 10 μL of 5 mg/mL MTT (3-[4,5-dimethylthiazole-2-yl]-2,5-diphenyltetrazolium bromide; Sigma) solution was added to each well and the cells were incubated for 4 h under the same condition. After the medium was aspirated from the well, 100 μL of dimethyl sulfoxide (DMSO) was added to dissolve MTT formazan and optical density (O.D.) was measured at 570 nm using a microplate reader (Bio-Rad 550; Molecular Devices, USA). The result is shown in FIG. 6.

Figure 6:
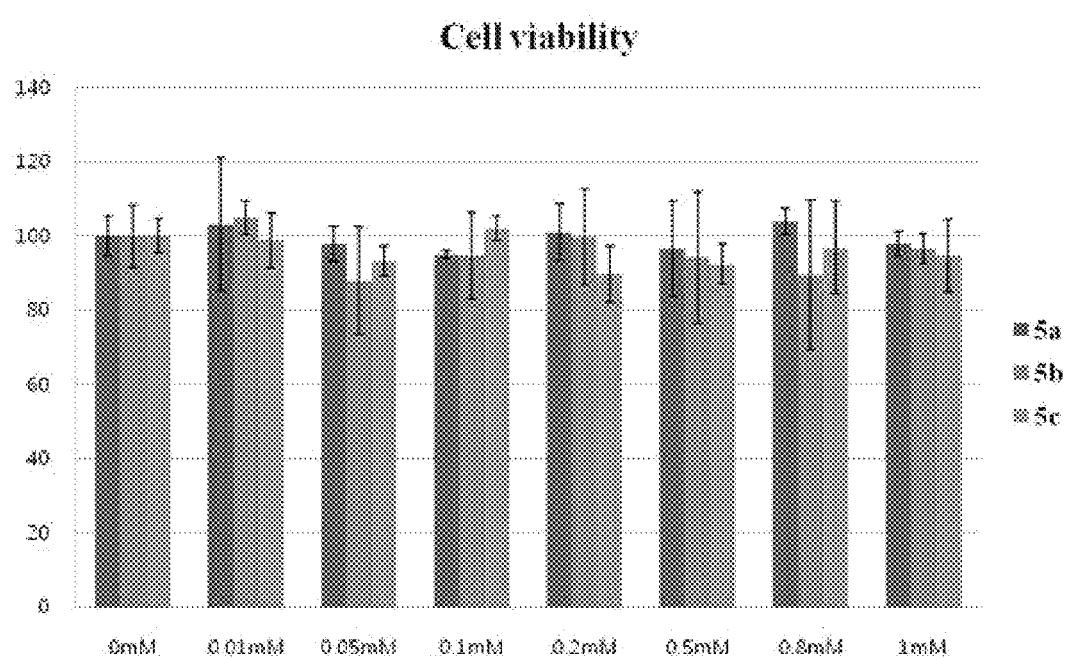
FIG. 6 shows cell viability measured for gadolinium complexes according to the present invention at various concentrations.

As seen from FIG. 6, the gadolinium complexes had no effect on cell proliferation and viability when incubated for 24 h. The cell viability of each test group is close to 100%, suggesting that the gadolinium complex contrast agents according to the present invention exhibit no cytotoxicity.

[References]

1. Kumar, K.; Chang, C. A.; Francesconi, L. C.; Dischino, D. D.; Malley, M. F.; Gougoutas, J. Z.; Tweedle, M. F. Synthesis, Stability, and Structure of Gadolinium(III) and Yttrium(III) Macrocylcic Poly(amino carboxylates). *Inorg. Chem.* 1994, 33 (16), 3567-75.

2. Kumar, K.; Tweedle, M. F.; Malley, M. F.; Gougoutas, J. Z. Synthesis, Stability, and Crystal Structure Studies of Some $Ca^{2+}$, $Cu^{2+}$, and $Zn^{2+}$ Complexes of Macrocylcic Polyamino Carboxylates. *Inorg. Chem.* 1995, 34 (26), 6472-80.

3. Martell, A. E.; Smith, R. M. Critical Stability Constants, Plenum, vol. 1: New York, 1974.

4. Schmitt-Willich, H.; Brehm, M.; Ewers, C. L.; Michl, G.; Muller-Fahrnow, A.; Petrov, 0.; Platzek, J.; Raduchel, B.; Sulzle, D. Synthesis and Physicochemical Characterization of a New Gadolinium Chelate: The Liver-Specific Magnetic Resonance Imaging Contrast Agent Gd-EOB-DTPA. *Inorg. Chem.* 1999, 38 (6), 1134-44.

5. Port, M.; Idee, J. M.; Medina, C.; Robic, C.; Sabatou, M.; Corot, C. Efficiency, thermodynamic and kinetic stability of marketed gadolinium chelates and their possible clinical consequences: a critical review. *Biometals* 2008, 21 (4), 469-90.

6. Uggeri, F.; Aime, S.; Anelli, P. L.; Botta, M.; Brocchetta, M.; de Haeen, C.; Ermondi, G.; Grandi, M.; Paoli, P. Nevel Contrast Agents for Magnetic Resonance Imaging. Synthesis and Characterization of the Ligand BOPTA and Its Ln(III) Complexes {Ln=Gd, La, Lu}. *Inorg. Chem.* 1995, 34 (3), 633-42.

7. Cacheris, W. P.; Quay, S. C.; Rocklage, S. M. The relationship between thermodynamics and toxicity of gadolinium complexes. *Magn. Reson. Imaging* 1990, 8 (4), 467-81.

8. Rohrer, M.; Bauer, H.; Mintorovitch, J.; Requardt, M.; Weinmann, H. J. Comparison of magnetic properties of MRI contrast media solutions at different magnetic field strengths. *Invest. Radiol.* 2005, 40 (11), 715-24.

9. Dutta, S.; Park, J. A.; Jung, J. C.; Chang, Y.; Kim, T. J. Gd-complexes of DTPA-bis(amide) conjugates of tranexamic acid and its esters with high relaxivity and stability for magnetic resonance imaging. *Dalton. Trans.* 2008 (16), 2199-206.

[Industrial Applicability]

As described above, the present invention provides a DO3A-tranexamic acid or its ester compound and a gadolinium complex prepared using the compound. A magnetic resonance imaging (MRI) contrast agent comprising the gadolinium complex prepared according to the present invention as an active ingredient has higher relaxivity as compared to the commercially available contrast agents for MRI. In addition, the MRI contrast agent according to the present invention has bifunctionality of liver-specific and blood-pool contrasting effect. Accordingly, since the MRI contrast agent comprising the gadolinium complex according to the present invention satisfies the requirements of an MRI contrast agent, it can be widely used as an MRI contrast agent and can provide enhanced contrasting effect as compared to the existing contrast agent.

The invention claimed is:

1. A DO3A-tranexamic acid or its ester compound, which is represented by the following Chemical Formula 1:

[Chemical Formula 1]

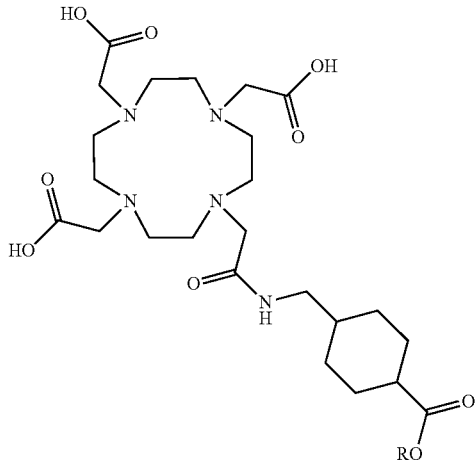

wherein R is selected from the group consisting of H, Me, Et, $(CH_2)_2OH$, $CH_2OMe$ and $CH_2CH=CH_2$.

2. A method of preparing the DO3A-tranexamic acid or its ester compound according to claim 1, comprising:
   a) adding bromoacetyl bromide to trans-4(aminomethyl)cyclohexaneethylcarboxylate hydrochloride with stirring;
   b) adding DO3A-($^t$BuO)$_3$ to the mixture with stirring;
   c) adding TFA to the mixture to deprotect a tert-butyl group;
   d) conducting silica gel chromatography after removing all of solvent under low pressure and dissolving the mixture in methanol; and
   e) drying the product obtained from the chromatography under vacuum state to obtain a DO3A-tranexamic acid or its ester compound.

3. The method according to claim 2, wherein allyl-trans-4 (aminomethyl)cyclohexaneethylcarboxylate hydrochloride is added instead of trans-4(aminomethyl)cyclohexaneethylcarboxylate hydrochloride in the step a).

4. A composition for a ligand (L) of a complex, which comprises the DO3A-tranexamic acid or its ester compound according to claim 1.

5. A complex comprising the DO3A-tranexamic acid or its ester compound according to claim 1 as a ligand (L) and a metal atom coordinately bonded to the ligand.

6. The complex according to claim 5, wherein the metal atom is gadolinium (Gd).

7. The complex according to claim 6, wherein the complex is represented by the Chemical Formula of [Gd(L)(H$_2$O).x CH$_3$COOH.yH$_2$O].

8. A magnetic resonance imaging (MRI) contrast agent comprising the complex according to claim 5 as an active ingredient.

9. The MRI contrast agent according to claim 8, wherein the contrast agent has bifunctionality of liver-specific and blood-pool contrasting effect.

10. The MRI contrast agent according to claim 8, wherein the contrast agent has high relaxivity and enhanced thermodynamic and kinetic stability.

* * * * *